US011495332B2

(12) United States Patent
Devarakonda et al.

(10) Patent No.: US 11,495,332 B2
(45) Date of Patent: Nov. 8, 2022

(54) AUTOMATED PREDICTION AND ANSWERING OF MEDICAL PROFESSIONAL QUESTIONS DIRECTED TO PATIENT BASED ON EMR

(71) Applicant: International Business Machines Corporation, Armonk, NY (US)

(72) Inventors: Murthy V. Devarakonda, Peekskill, NY (US); Preethi Raghavan, Cambridge, MA (US); Paul C. Tang, Los Altos, CA (US)

(*) Notice: Subject to any disclaimer, the term of this patent is extended or adjusted under 35 U.S.C. 154(b) by 221 days.

(21) Appl. No.: 15/856,912

(22) Filed: Dec. 28, 2017

(65) Prior Publication Data

US 2019/0206517 A1 Jul. 4, 2019

(51) Int. Cl.
| | |
|---|---|
| *G16H 10/20* | (2018.01) |
| *G16H 10/60* | (2018.01) |
| *G06F 16/332* | (2019.01) |
| *G16H 15/00* | (2018.01) |
| *G16H 50/70* | (2018.01) |
| G16H 50/20 | (2018.01) |

(52) U.S. Cl.
CPC ........ *G16H 10/20* (2018.01); *G06F 16/3329* (2019.01); *G16H 10/60* (2018.01); *G16H 15/00* (2018.01); *G16H 50/70* (2018.01); G16H 50/20 (2018.01)

(58) Field of Classification Search
CPC .......... G06F 19/30; G06F 19/32; G06F 19/34; G06F 19/36; G06F 16/3329; G06Q 50/22; G06Q 50/24; G16H 10/20; G16H 15/00; G16H 50/70; G16H 10/60; G16H 50/20
See application file for complete search history.

(56) References Cited

U.S. PATENT DOCUMENTS

| | | |
|---|---|---|
| 6,401,072 B1 | 6/2002 | Haudenschild et al. |
| 7,433,827 B2 | 10/2008 | Rosenfeld et al. |
| 9,081,879 B2 | 7/2015 | Edwin |
| 9,492,341 B2 | 11/2016 | Huster et al. |

(Continued)

OTHER PUBLICATIONS

List of IBM Patents or Patent Applications Treated as Related, Feb. 19, 2018, 2 pages.

(Continued)

*Primary Examiner* — Robert W Morgan
*Assistant Examiner* — Shyam M Goswami
(74) *Attorney, Agent, or Firm* — Stephen J. Walder, Jr.

(57) ABSTRACT

A mechanism is provided in a data processing system comprising a processor and a memory, the memory comprising instructions that are executed by the processor to specifically configure the processor to implement a question prediction and answering engine for predicting questions a medical professional is attempting to answer. An interaction monitoring component monitors interaction of a medical professional with a patient electronic medical record (EMR). A question selection component selects a set of questions the medical professional is attempting to obtain an answer to from the patient EMR. The question prediction and answering engine analyzes the patient EMR to generate a set of answers to the set of questions from at least a portion of the patient EMR and outputs a report correlating the set of questions and the set of answers to the medical professional.

18 Claims, 4 Drawing Sheets

(56) References Cited

U.S. PATENT DOCUMENTS

| | | | |
|---|---|---|---|
| 9,690,861 | B2 | 6/2017 | Boloor et al. |
| 2002/0065686 | A1* | 5/2002 | Monteleone ............ G16H 10/60 705/3 |
| 2004/0122701 | A1 | 6/2004 | Dahlin et al. |
| 2005/0159987 | A1 | 7/2005 | Rosenfeld et al. |
| 2006/0085223 | A1 | 4/2006 | Anderson et al. |
| 2006/0122869 | A9 | 6/2006 | Rosenfeld et al. |
| 2009/0222286 | A1 | 9/2009 | Elsholz |
| 2009/0228303 | A1 | 9/2009 | Faulkner et al. |
| 2009/0281839 | A1 | 11/2009 | Lynn et al. |
| 2012/0089419 | A1 | 4/2012 | Huster et al. |
| 2012/0215560 | A1 | 8/2012 | Ofek et al. |
| 2012/0239434 | A1 | 9/2012 | Breslow et al. |
| 2013/0226601 | A1 | 8/2013 | Razmi et al. |
| 2013/0226617 | A1 | 8/2013 | Mok et al. |
| 2014/0052465 | A1 | 2/2014 | Madan et al. |
| 2014/0244309 | A1 | 8/2014 | Francois |
| 2014/0310016 | A1 | 10/2014 | Kenney et al. |
| 2014/0337052 | A1 | 11/2014 | Pellini et al. |
| 2015/0058039 | A1 | 2/2015 | Shiloh |
| 2015/0066520 | A1* | 3/2015 | Leon ................ G06F 19/3456 705/2 |
| 2015/0161241 | A1 | 6/2015 | Haggar et al. |
| 2015/0193583 | A1* | 7/2015 | McNair ................. G16H 50/20 705/2 |
| 2015/0261849 | A1 | 9/2015 | Chu-Carroll et al. |
| 2016/0019299 | A1 | 1/2016 | Boloor et al. |
| 2016/0019352 | A1 | 1/2016 | Cohen et al. |
| 2016/0098456 | A1 | 4/2016 | Contreras et al. |
| 2016/0110523 | A1 | 4/2016 | Francois |
| 2016/0147727 | A1 | 5/2016 | Allen et al. |
| 2017/0027787 | A1 | 2/2017 | Huster et al. |
| 2017/0178266 | A1 | 6/2017 | Schmidt |
| 2017/0185920 | A1* | 6/2017 | Chawla .................. G06F 16/00 |
| 2017/0286626 | A1 | 10/2017 | Jayakumar et al. |
| 2019/0156921 | A1* | 5/2019 | Kohli ...................... G06F 40/30 |

OTHER PUBLICATIONS

"The Era of Cognitive Systems: An inside look at IBM Watson and how it works", IBM Corporation, IBM Software Group, Whitepaper, IBM Watson Solutions, Sep. 2012, 19 pages.

Abedtash, Hamed, "An Interoperable Electronic Medical Record-Based Platform for Personalized Predictive Analytics", Indiana University-Purdue University Indianapolis (IUPUI), Doctor of Philosophy in the School of Informatics and Computing, Doctoral Dissertation, Jul. 2017, 184 pages.

Alemzadeh, Homa et al., "An NLP-based Cognitive System for Disease Status Identification in Electronic Health Records", IEEE, 2017 IEEE EMBS International Conference on Biomedical & Health Informatics (BHI), Feb. 16-19, 2017, 4 pages.

Deleger, Louise et al., "Building Gold Standard Corpora for Medical Natural Language Processing Tasks", American Medical Informatics Association, AMIA Annual Symposium Proceedings, vol. 2012, Nov. 3, 2012, pp. 144-153.

Demner-Fushman, Dina et al., "What can Natural Language Processing do for Clinical Decision Support?", National Institutes of Health, Author Manuscript, J Biomed Inform., vol. 42, No. 5, Oct. 2009, pp. 760-772.

Taranu, Ionut, "Data mining in healthcare: decision making and precision", Database Systems Journal, vol. VI, Issue Apr. 2015, Publication date: May 5, 2016, 8 pages.

\* cited by examiner

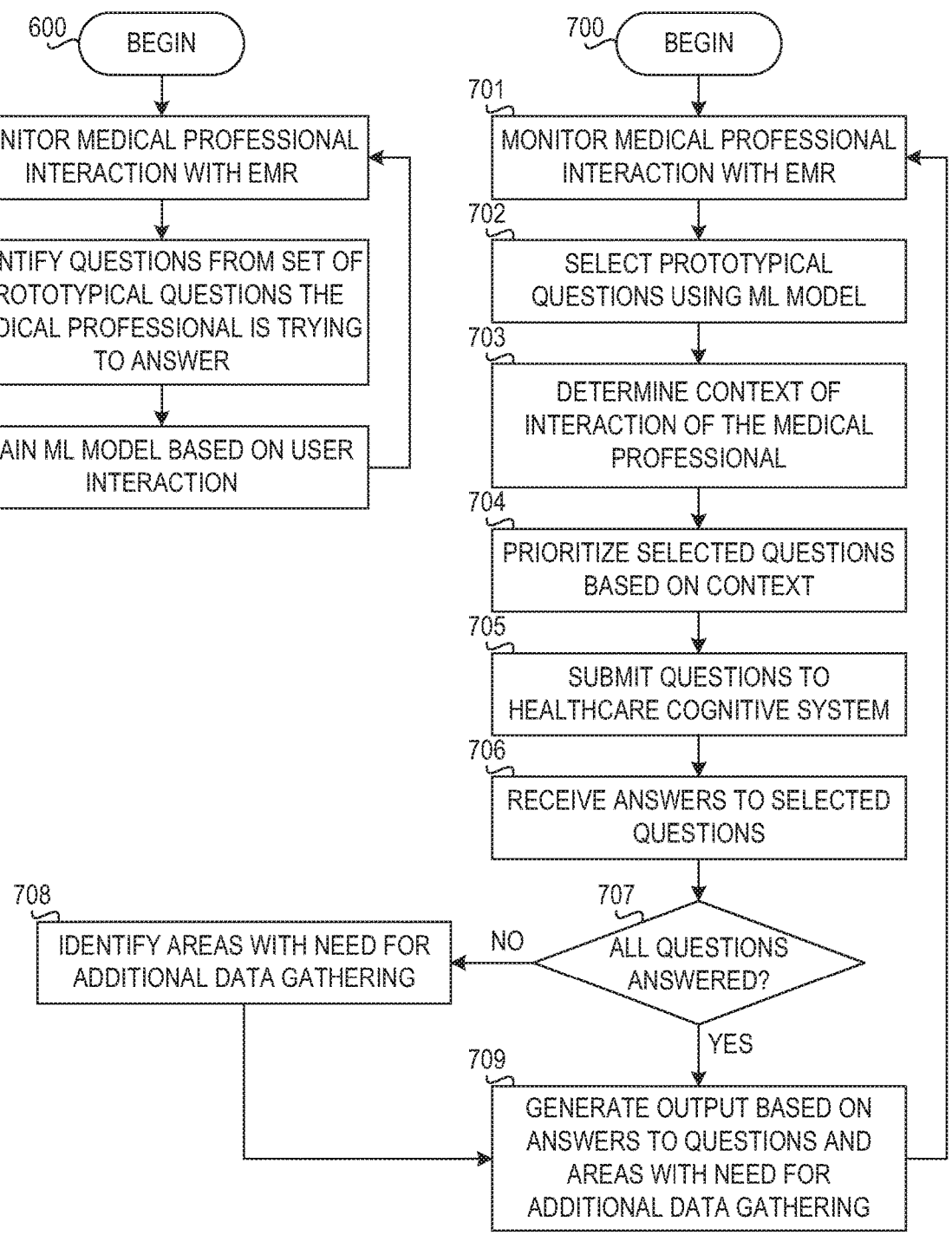

AUTOMATED PREDICTION AND ANSWERING OF MEDICAL PROFESSIONAL QUESTIONS DIRECTED TO PATIENT BASED ON EMR

BACKGROUND

The present application relates generally to an improved data processing apparatus and method and more specifically to mechanisms for automated prediction and answering of medical professional questions directed to a patient based on the patient's electronic medical record.

An electronic health record (EHR) or electronic medical record (EMR) is the systematized collection of patient and population electronically-stored health information in a digital format. These records can be shared across different health care settings. Records are shared through network-connected, enterprise-wide information systems or other information networks and exchanges. EMRs may include a range of data, including demographics, medical history, medication and allergies, immunization status, laboratory test results, radiology images, vital signs, personal statistics like age and weight, and billing information.

EMR systems are designed to store data accurately and to capture the state of a patient across time. It eliminates the need to track down a patient's previous paper medical records and assists in ensuring data is accurate and legible. It can reduce risk of data replication as there is only one modifiable file, which means the file is more likely up to date, and decreases risk of lost paperwork. Due to the digital information being searchable and in a single file, EMRs are more effective when extracting medical data for the examination of possible trends and long term changes in a patient. Population-based studies of medical records may also be facilitated by the widespread adoption of EMRs.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising a processor and a memory, the memory comprising instructions that are executed by the processor to specifically configure the processor to implement a question prediction and answering engine for predicting questions a medical professional is attempting to answer. The method comprises monitoring, by an interaction monitoring component executing within the question prediction and answering engine, interaction of a medical professional with a patient electronic medical record (EMR). The method further comprises selecting, by a question selection component executing within the question prediction and answering engine, a set of questions the medical professional is attempting to obtain an answer to from the patient EMR. The method further comprises analyzing, by the question prediction and answering engine, the patient EMR to generate a set of answers to the set of questions from at least a portion of the patient EMR. The method further comprises outputting, by the question prediction and answering engine, a report correlating the set of questions and the set of answers to the medical professional.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 6 is a flowchart of a mechanism for personalized interaction in accordance with an illustrative embodiment; and FIG. 7 is a flowchart illustrating operation of a mechanism for question prediction and answering in accordance with an illustrative embodiment.

DETAILED DESCRIPTION

Figure 1:
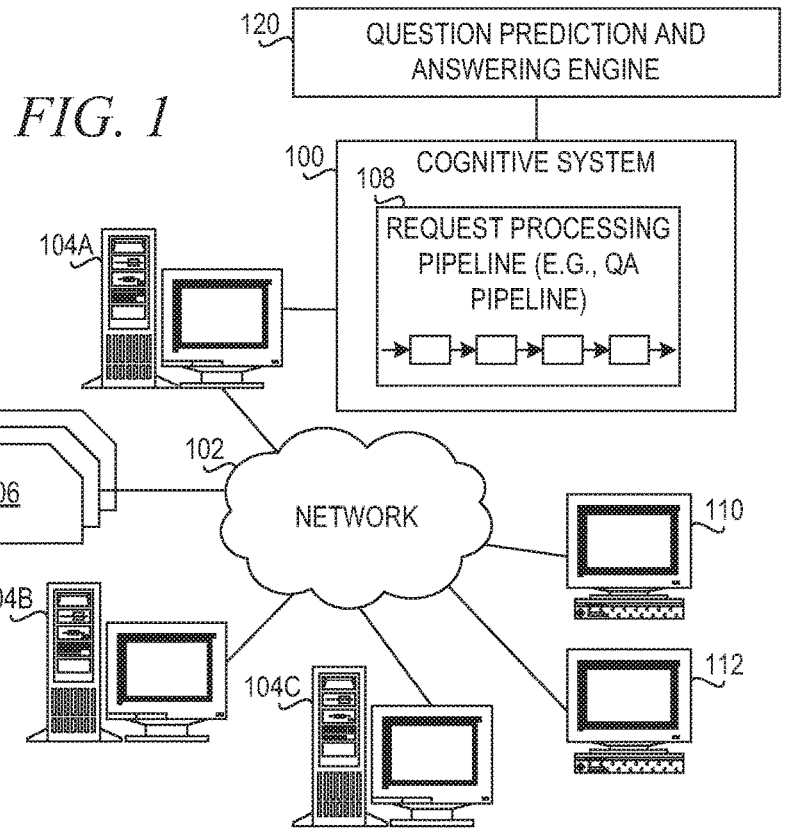
FIG. 1 depicts a schematic diagram of one illustrative embodiment of a cognitive healthcare system in a computer network.

Due to government regulations and advancement in computing technology, many professionals and organizations store patient information in electronic medical records. As the size of these electronic medical records (EMRs) increases, it becomes more difficult for medical professionals to locate and disambiguate information in the EMRs to identify the portions that are of particular relevance to the patient medical conditions being investigated by the medical professional. For example, if the medical professional is treating a patient during an office visit, the medical professional may need to look through the patient's medical history, as stored in the EMR, to identify the particular portions that are relevant to the particular medical issue that the patient is complaining of and/or identify the portions that are of particular importance to previous treatment plans that were applied to the patient. This may be a daunting task, which prior to the implementation of EMRs was a manual task, especially when integration of EMRs from a variety of different sources of information becomes more prolific. That is, when a patient's complied EMRs store information from a variety of different hospitals, pharmacies, emergency clinics, doctors, specialists, etc., it may be difficult to identify what information in these EMRs is of particular relevance to the patient's current medical issues and the particular plan of treatment previously prescribed to the patient. Thus, there is a high likelihood that some pertinent information may be missed. Moreover, the complexity of searching through EMRs to find relevant information leads to frustration on the part of the medical professional.

During a patient visit, physicians have a set of questions in mind and attempt to find answers to those questions. The questions and answers are dynamic, based on the visit, context, and patient's current status. While some questions can only be answered by a patient or through an examination at the visit, many can be answered through a careful review of the patient record. For example, the physician may ask the following question: "Did the patient have an allergy reaction for a certain drug/drug-class that I am planning to order?" It saves a lot of time, avoids unnecessary testing, or even may save lives if a system can anticipate a physician's questions at a point of a patient visit (or at a chart review) and answer them with data from the patient's EMR, if the answers exist in the EMR, and raise the need for additional data gathering if answers are not in the record.

The illustrative embodiments provide mechanisms that emulate the thinking of a medical professional with regard to reviewing a patient's EMR to identify pertinent information for treating a patient. In particular, the mechanisms monitor the medical professional's interaction with the patient's EMR and predicts, based on supervised learning, what questions (potentially from a set of prototypical questions) the medical professional is likely attempting to obtain an answer for from the patient EMR. The questions may be prioritized based on a variety of factors, which may include the context of the current interaction with the patient EMR and the type of interaction of the medical professional (e.g., hovering a cursor over a particular location in the EMR, zooming in on a portion of an image in the EMR, etc.). The questions may be answered from information present in the patient EMR. The questions/answers may then be presented to the medical professional.

The illustrative embodiments alleviate the burden and frustration of a medical professional when searching through past medical information about the patient in a voluminous patient EMR to find information pertinent to the questions that a medical professional is most likely wanting to have answered.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
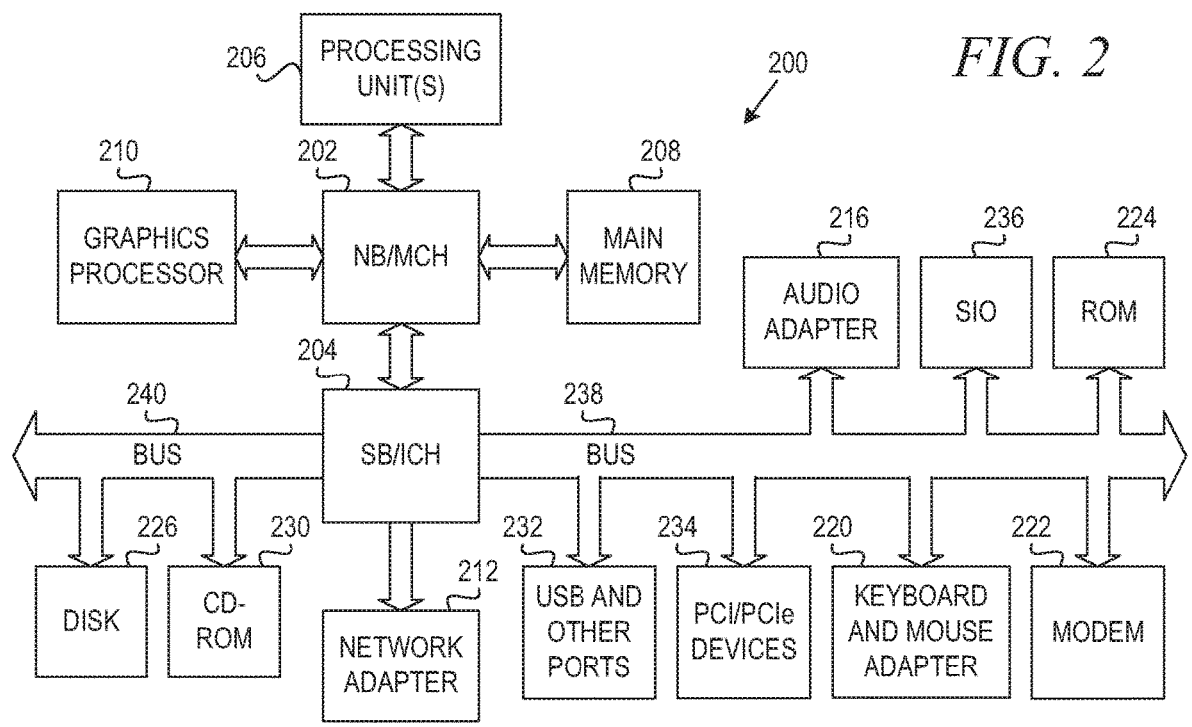
FIG. 2 is a block diagram of an example data processing system in which aspects of the illustrative embodiments are implemented.
Figure 3:
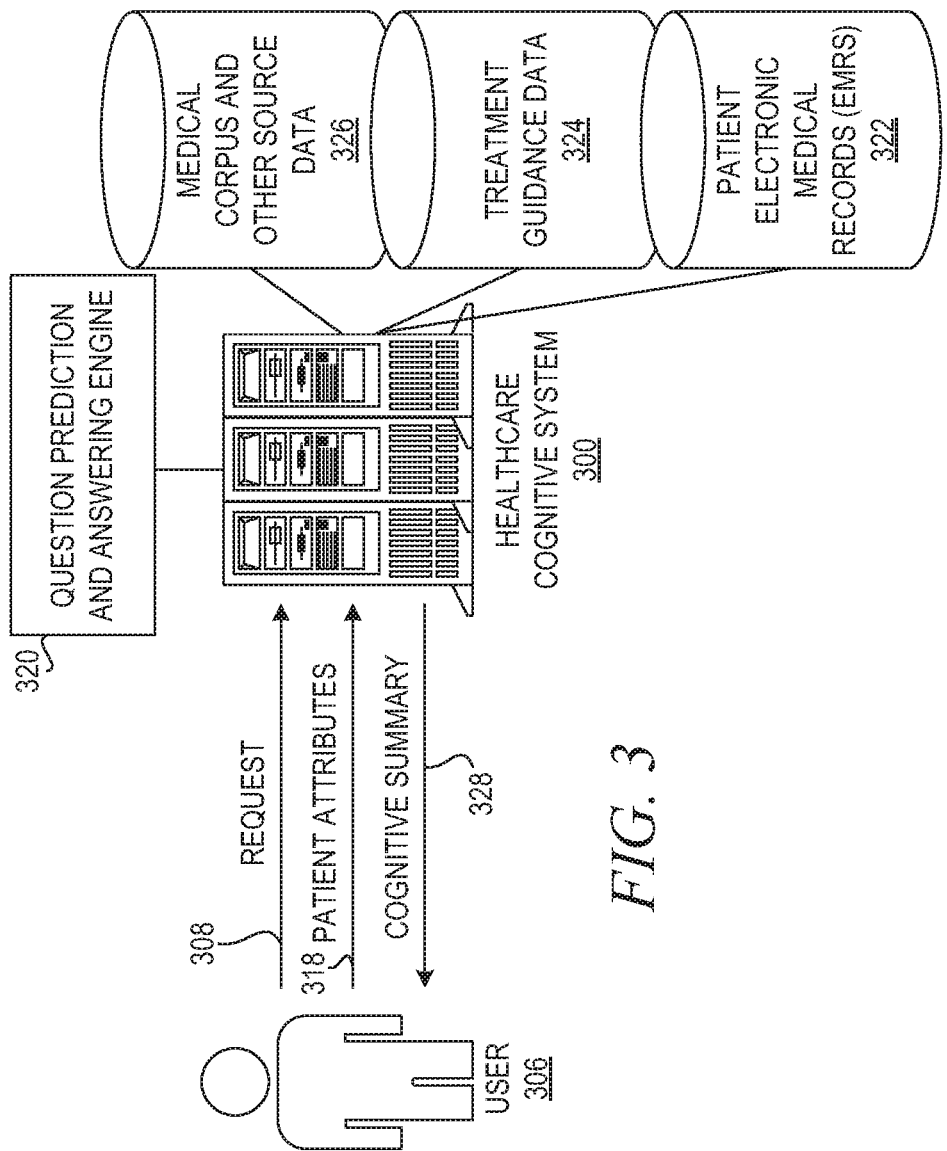
FIG. 3 is an example diagram illustrating an interaction of elements of a healthcare cognitive system in accordance with one illustrative embodiment.

As noted above, the present invention provides mechanisms for graphical presentation of relevant information from electronic medical records. The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for graphical presentation of relevant information from electronic medical records.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to automated prediction and answering of medical professional questions directed to a patient based on the patient's electronical medical record.

It is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding

Ingest and process vast amounts of structured and unstructured data

Generate and evaluate hypothesis

Weigh and evaluate responses that are based only on relevant evidence

Provide situation-specific advice, insights, and guidance
Improve knowledge and learn with each iteration and interaction through machine learning processes
Enable decision making at the point of impact (contextual guidance)
Scale in proportion to the task
Extend and magnify human expertise and cognition
Identify resonating, human-like attributes and traits from natural language
Deduce various language specific or agnostic attributes from natural language
High degree of relevant recollection from data points (images, text, voice) (memorization and recall)
Predict and sense with situational awareness that mimic human cognition based on experiences
Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to the cognitive system, which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

Question answering (QA) from electronic medical records (EMRs) has significantly different challenges when compared to open-domain, fact-based QA. Automatically answering prototypical questions asked by a physician requires the system to first address multiple NLP problems like relation detection, temporal reasoning, and discourse analysis. These challenges are brought on by the corpus size being limited to the patient's EMR, no redundancy in facts, and the longitudinal and domain-specific nature of information centered around a patient. In light of this, it has been shown that pipelined approaches, which perform retrieval followed by candidate ranking, like the Watson QA pipeline, do not always perform well on EMR data. There are a number of alternate approaches that may be applied, including treating QA as a reading comprehension task, organizing unstructured data as a graph and inferring the answer using graphical methods, or creating a knowledge bank from unstructured text that one can query using a structured language to obtain the answer.

Machine learning for reading comprehension has been investigated to answer questions from sources such as Wikipedia, news articles, and fictional stories. A machine is said to comprehend a passage of text if, for any question regarding that text that can be answered correctly by a majority of native speakers, that machine can provide a string that those speakers would agree answers that question. Answering these questions usually requires the machine to understand a passage or a body of text and infer the correct answer. Such systems are suited to answering patient-specific questions asked by physicians where the answer may require the system to identify and reason with entities and relations found in a clinical note. The Stanford Question Answering Dataset (SquAD) reading comprehension task is one such example of a system answering questions about paragraphs from Wikipedia. A limitation of formulating the QA problem as a reading comprehension task is that it does not work well on longitudinal collection of documents, such as an EMR, where there is lack of discourse continuity.

Another approach to the problem is organizing EMR data as a graph and inferring the correct answer on this graphical structure. Here, medical entities in the clinical note are nodes, connections between nodes are based on the relationship between the medical entities. The graph structure can then be queried using semantic query languages or various inference mechanisms. This also maps to the problem of textual inference or entailment that provides tools for producing a semantic representation from arbitrary text and for doing inference upon such representations. This allows the system to first address individual NLP tasks like entity and relation detection, followed by learning to predict entailment using graph alignment or classification-based approaches. Alternately, deep neural networks that use memory units like recurrent neural networks (RNNs) and long short-term memories (LSTMs) are powerful sequence predictors that can be efficiently trained to learn to do inference over long term dependencies in the text and learn.

A deep semantic understanding of physician questions is necessary for an effective EMR QA system because data is stored in both unstructured text and structured databases. This may be achieved by semantic parsing of questions to map them to a machine-interpretable logical form such as lambda calculus or structured query language (SQL) queries. An alternate approach is to induce a machine learning objective function that maps questions to queries over a database of facts extracted from a large body of text like the web. It is possible to then use handcrafted features that take into consideration lexical and syntactic patterns occurring in the question text as well as a database. The challenge here is two-fold—(1) parsing the extensive body of text in the EMR and structuring it into a database and (2) parsing the question into a structured query to fetch information from the database.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety.

The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like.

In some illustrative embodiments, the cognitive system 100 and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

The cognitive system described above is an example embodiment. The cognitive system may be more general or may include other QA technologies. For example, the cognitive system may use a knowledge graph or frames and a search that uses these representations to find answers to the questions. Other QA system technologies may be used without departing from the spirit and scope of the illustrative embodiments described herein. That is, the present invention is not to be limited to any specific QA system technologies described herein.

In the context of the present invention, cognitive system 100 may provide a cognitive functionality for assisting with healthcare based operations. For example, depending upon the particular implementation, the healthcare based operations may comprise patient diagnostics medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a question prediction and answering engine 120 that emulates the thinking of a medical professional with regard to reviewing a patient's EMR to identify pertinent information for treating a patient. Question prediction and answering engine 120 monitors the medical professional's interaction with the EMR and predicts what questions the medical professional is likely attempting to obtain an answer for from the patient EMR. Question prediction and answering engine 120 prioritizes the questions based on a variety of factors, which may include the context of the current interaction with the patient EMR and the type of interaction of the medical professional.

Question prediction and answering engine 120 then attempts to answer the questions by submitting them to cognitive system 100. Question prediction and answering engine 120 also identifies questions for which no answer is found in the patient EMR and determines areas with need for additional data gathering. Question prediction and answering engine 120 then generates an output presenting the answers and the determined areas with need for additional data gathering to the medical professional.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (1/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide a cognitive summary of EMR data for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, the user 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, symptoms, and other pertinent information obtained from responses to questions or information obtained from medical equipment used to monitor or gather data about the condition of the patient. Any information about the patient that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a cognitive summary of EMR data 328 to the user 306 to assist the user 306 in treating the patient based on their reported symptoms and other information gathered about the patient. The healthcare cognitive system 300 operates on the request 308 and patient attributes 318 utilizing information gathered from the medical corpus and other source data 326, treatment guidance data 324, and the patient EMRs 322 associated with the patient to generate cognitive summary 328. The cognitive summary 328 may be presented in a ranked ordering with associated supporting evidence, obtained from the patient attributes 318 and data sources 322-326, indicating the reasoning as to why portions of EMR data 322 are being provided.

For example, based on the request 308 and the patient attributes 318, the healthcare cognitive system 300 may operate on the request, such as by using a QA pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve data, generate candidate answers to the input question, and score these candidate answers based on supporting evidence found in the data sources 322-326.

In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients in a manner (structured, unstructured, or a mix of structured and unstructured formats) that the information may be retrieved and processed by the healthcare cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient, the patient's corresponding EMRs 322 from this patient repository may be retrieved by the healthcare cognitive system 300 and searched/processed to generate cognitive summary 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In accordance with the illustrative embodiments herein, the healthcare cognitive system 300 is augmented to include a question predication and answering engine 320 that emulates the thinking of a medical professional with regard to reviewing a patient's EMR 322 to identify pertinent information for treating a patient. Question prediction and answering engine 320 monitors the medical professional's interaction with the EMR 322 and predicts what questions the medical professional is likely attempting to obtain an answer for from the patient EMR 322. Question prediction and answering engine 320 prioritizes the questions based on a variety of factors, which may include the context of the current interaction with the patient EMR and the type of interaction of the medical professional. Question prediction and answering engine 320 then attempts to answer the questions by submitting them to cognitive system 300. Question prediction and answering engine 320 also identifies questions for which no answer is found in the patient EMR and determines areas with need for additional data gathering. Question prediction and answering engine 320 then generates an output presenting the answers and the determined areas with need for additional data gathering to the medical professional.

Figure 4:
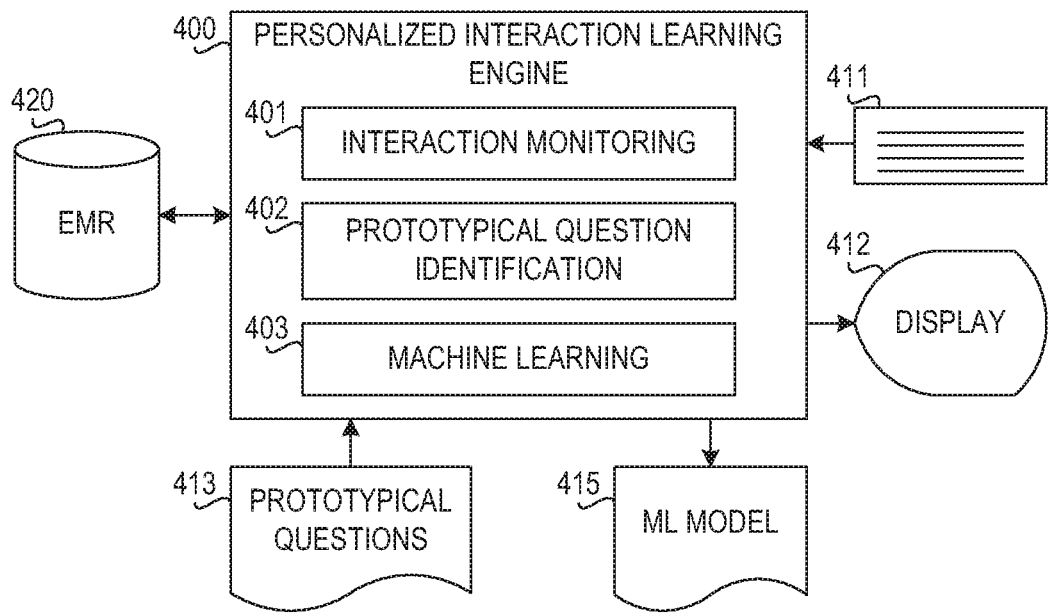
FIG. 4 is a block diagram illustrating a personalized interaction learning engine in accordance with an illustrative embodiment.

FIG. 4 is a block diagram illustrating a personalized interaction learning engine in accordance with an illustrative embodiment. Personalized interaction learning engine 400 includes interaction monitoring component 401, prototypical question identification component 402, and machine learning component 403. Interaction monitoring component 401 monitors a user interactions with electronic medical records 420 using input devices 411 and display 412. Input devices 411 may include a keyboard, a mouse, or other known or future input devices. As the user interacts with EMR data 420, interaction monitoring component 401 detects information, such as questions asked by the user, which portions of the EMR the user views, the order in which the user asks questions, the order in which the user views EMR portions, whether the user hovers the mouse cursor over a particular location in the EMR, whether the user zooms in on a portion of an image in the EMR, etc.

Prototypical question identification component 402 examines the user interaction patterns from interaction monitoring component 401 and correlates those patterns to questions within a set of prototypical questions 413. In one embodiment, prototypical question identification component 402 examines questions entered by the user into input device 411. Prototypical question identification component 402 may then identify questions from the set of prototypical questions 413 that most closely match the question entered by the user.

In another embodiment, prototypical question identification component 402 examines features from the user interaction patterns and treats them as if they are evidence passages or portions for candidate answers to a question. Prototypical question identification component 402 then determines which questions from prototypical questions 413 the evidence passages would answer with high confidence.

In another embodiment, prototypical question identification component 402 may submit each question from prototypical questions 413 to a cognitive question answering system to determine a set of evidence passages or portions that support the high confidence answers to each question. Prototypical question identification component 402 may then determine which sets of evidence passages or portions match the user interaction patterns.

In this way, prototypical question identification component 402 correlates user interaction patterns to questions in prototypical questions 413. Machine learning component 403 then trains machine learning (ML) model 415 based on these correlations. Thus, ML model 415 is configured to receive a user interaction pattern and determine one or more questions from prototypical questions 413 that most closely correlate to the pattern.

Prototypical questions 413 comprise questions that medical professionals are likely to ask regarding treatment of a patient. There may be a different set of prototypical questions 413 for each outcome the medical professional is attempting to control or each medical condition for which the patient is being treated. Medical resource documents may be processed to identify particular types of these prototypical questions that are likely associated with a particular medical condition, which may be learned through a supervised learning process. This indicates the likely types of questions that a medical professional is likely to ask about the patient when treating the patient for a particular medical condition.

Machine learning component 403 may use a supervised machine learning technique. Supervised learning is the machine learning task of inferring a function from labeled training data. The training data consist of a set of training examples. In supervised learning, each example is a pair consisting of an input object (typically a vector) and a desired output value (also called the supervisory signal). A supervised learning algorithm analyzes the training data and produces an inferred function, which can be used for mapping new examples. An optimal scenario will allow for the algorithm to correctly determine the class labels for unseen instances. For example, while the medical professional is interacting with EMR 420, personalized interaction learning engine 400 may prompt the medical professional with the prototypical questions 413 to select a question for which the medical is attempting to find an answer. As the medical professional continues the interaction and provides more instances of correlating prototypical questions 413 with user interaction patterns, ML model 415 will become more accurate.

ML model 415 may be trained using any known or future machine learning technique, such as linear regression, logistic regression, clustering, genetic or evolutionary algorithms, decision tree learning, or the like. In one embodiment, ML model 415 is a linear regression machine learning model. Alternatively, ML model 415 may use other machine learning techniques, such as unsupervised or semi-supervised machine learning techniques.

Figure 5:
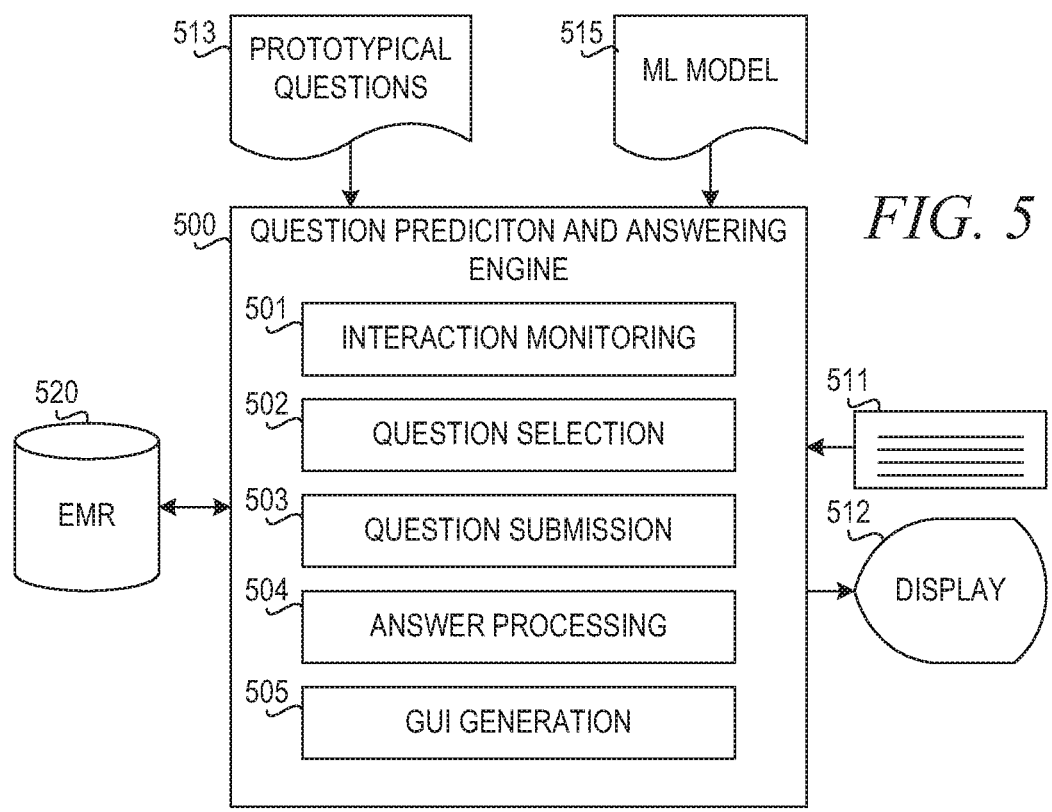
FIG. 5 is a block diagram illustrating a question prediction and answering engine in accordance with an illustrative embodiment.

FIG. 5 is a block diagram illustrating a question prediction and answering engine in accordance with an illustrative embodiment. Question prediction and answering engine 500 includes interaction monitoring component 501, question selection component 502, question submission component 503, answer processing component 504, and graphical user interface (GUI) generation component 505. Interaction monitoring component 501 monitors a user interactions with electronic medical records 520 using input devices 511 and display 512. Input devices 511 may include a keyboard, a mouse, or other known or future input devices. As the user interacts with EMR data 520, interaction monitoring component 501 detects information, such as questions asked by the user, which portions of the EMR the user views, the order in which the user asks questions, the order in which the user views EMR portions, whether the user hovers the mouse cursor over a particular location in the EMR, whether the user zooms in on a portion of an image in the EMR, etc.

Interaction monitoring component 501 may determine a context of a patient treatment and a context of the user interaction. For example, interaction monitoring component 501 may determine a medical condition or outcome the medical professional is attempting to control. Interaction monitoring component 501 may also determine a context of the interaction of the medical professional. For example, interaction monitoring component 501 may determine whether the medical professional is hovering a cursor over a particular location in the EMR 520, zooming in on a portion of an image in the EMR 520, etc.

Question selection component 502 selects questions from prototypical questions 513 using ML model 515 based on the user interaction patterns from 501. That is, question selection component 502 configured with ML model 515 predicts questions the medical professional is attempting to find answers for based on the medical professional's interaction patterns. As stated above, ML model 515 is configured to receive a user interaction pattern from interaction monitoring component 501 and determine one or more questions from prototypical questions 513 that most closely correlate to the pattern.

Question selection component 502 may also prioritize the selected questions form prototypical questions 513 based on a variety of factors, which may include the context of the current interaction with the patient EMR 520 and the context of the interaction of the medical professional. In one embodiment, ML model 515 returns a list of questions from prototypical questions 513 with associated confidence values. For a given question, its confidence value represents a confidence that the question is one that the medical professional is attempting to answer through the medical professional's interaction with the EMR 520. Thus, the prioritization may comprise ranking the returned questions by confidence value.

Question submission component 503 submits the prioritized list of questions to the EMR 520 or a cognitive question answering system (not shown in FIG. 5) to receive answers to the questions from EMR 520. A cognitive question answering system may attempt to answer the questions using natural language and cognitive techniques as discussed above with reference to FIGS. 1-3.

Answer processing component 504 processes the answers to the questions. In one embodiment, answer processing component 504 modifies the form of the answers to be included in a graphical user interface (GUI). In another embodiment, answer processing component 504 identifies questions for which an answer could not be found in EMR data 520.

GUI generation component 505 generates a GUI to present the answers to the questions to the medical professional as a tailored, cognitive information retrieval. GUI generation component 505 may present the answers in the order of the prioritized questions. GUI generation component 505 may simply present the answers or may present the answers in association with the questions they answer. GUI generation component 505 may also provide links to the EMR 520 in association with the answers. Furthermore, GUI generation component 505 may present areas needing additional data retrieval based on the answers for which an answer could not be found in the EMR data 520.

FIG. 6 is a flowchart of a mechanism for personalized interaction in accordance with an illustrative embodiment. Operation begins (block 600), and the mechanism monitors medical professional interactions with the electronic medical record (EMR) (block 601). As the user interacts with the EMR data, the mechanism detects information, such as questions asked by the user, which portions of the EMR the user views, the order in which the user asks questions, the order in which the user views EMR portions, whether the user hovers the mouse cursor over a particular location in the EMR, whether the user zooms in on a portion of an image in the EMR, etc.

The mechanism then identifies questions from a set of prototypical questions the medical professional is attempting to answer (block 602). The mechanism may identify questions by prompting the medical professional to select a question from the set of prototypical questions. Alternatively, the mechanism may receive labeling from a subject matter expert (SME). In another embodiment, the mechanism identifies questions by submitting the prototypical questions to a question answering cognitive system, which returns evidence passages or portions from the EMR data that answers the questions with some confidence. The mechanism may then match the evidence passages or portions of the EMR data to the detected user interaction patterns.

Next, the mechanism trains a machine learning (ML) model based on the user interactions and the identified questions from the set of prototypical questions (block 603). The mechanism may use supervised, semi-supervised, or unsupervised machine learning techniques. The ML model is configured to receive a user interaction pattern for a medical professional interacting with a patient EMR and return one or more questions from a set of prototypical questions and a confidence value for each question. Thereafter, operation returns to block 601 to continue monitoring the medical professional's interaction with the EMR data.

FIG. 7 is a flowchart illustrating operation of a mechanism for question prediction and answering in accordance with an illustrative embodiment. Operation begins (block 700), and the mechanism monitors medical professional interaction with a patient EMR (block 701). The mechanism selects prototypical questions using a ML model based on the detected user interaction patterns (block 702). The mechanism determines a context of the interaction of the medical professional (block 703) and prioritizes the selected questions based on the context (block 704).

Then, the mechanism submits the selected questions to a healthcare cognitive system to find answers to the questions within the patient EMR (block 705) and receives answers to the selected questions form the patient EMR (block 706). The mechanism determines whether all questions were answered from the patient EMR (block 707). If at least one question was not answered, then the mechanism identifies areas with need for additional data gathering (block 708). Thereafter, of if all questions are answered from the patient EMR in block 707, the mechanism generates output based on answers to questions and areas with need for additional data gathering, if any (block 709). The output may comprise a graphical user interface (GUI) with the selected questions in priority order with the respective answers from the patient EMR. Alternatively, the output may comprise a GUI with the answers, highlighting or linking the portions of the patient EMR containing the answers. The output may also indicate the areas of the patient EMR that require additional data gathering, such as tests, forms, physiological readings, etc. Thereafter, operation returns to block 701 to continue monitoring the medical professional's interaction with the patient EMR.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to specifically configure the processor to implement a question prediction and answering engine for predicting questions a medical professional is attempting to answer, the method comprising:

training, by a personalized interaction learning engine, a machine learning model, comprising:
  monitoring interaction of a user with an electronic medical record (EMR) to identify one or more natural language questions entered by the user into an input device and submitted to a cognitive question answering system;
  identifying a first set of questions within a predetermined set of questions that match the one or more natural language questions entered by the user;
  correlating the one or more natural language questions entered by the user to the first set of questions; and
  training the machine learning model based on the correlation between the one or more natural language questions entered by the user and the first set of questions;
monitoring, by an interaction monitoring component executing within the question prediction and answering engine, interaction of a medical professional with a patient electronic medical record (EMR) to identify a medical professional interaction pattern;
applying, by a question selection component executing within the question prediction and answering engine, the machine learning model to the medical professional interaction pattern to select a second set of questions, from the predetermined set of questions, the medical professional is attempting to obtain an answer to from the patient EMR, wherein the machine learning model is configured to receive the medical professional interaction pattern and determine the second set of questions that correlate to the medical professional interaction pattern;
submitting, by a question submission component executing within the question prediction and answering engine, the second set of questions to the cognitive question answering system;
receiving, by an answer processing component executing within the question prediction and answering engine, answers to the second set of questions from the cognitive question answering system based on the patient EMR;
processing, by the answer processing component, the answers to the second set of questions to generate a set of answers to the second set of questions from at least a portion of the patient EMR; and
outputting, by the question prediction and answering engine, a report correlating the second set of questions and the set of answers to the medical professional at least by generating a graphical user interface (GUI) to present the answers to the second set of questions to the medical professional as a tailored, cognitive information retrieval, wherein the GUI presents areas needing additional data retrieval based on questions in the second set of questions for which an answer could not be found in the patient EMR.

2. The method of claim 1, wherein monitoring the interaction of the medical professional with the EMR comprises detecting an interaction from the set consisting of portions of the EMR the medical professional views, an order in which the medical professional views EMR portions, the medical professional hovering a cursor over a particular location in the EMR, or the medical professional zooming on the at least a portion of the patient EMR.

3. The method of claim 1, further comprising:
determining a context of the interaction of the medical professional with the patient EMR; and
prioritizing the second set of questions based on the determined context.

4. The method of claim 3, wherein determining the context of the interaction comprises detecting an interaction from the set consisting of portions of the EMR the medical professional views, an order in which the medical professional views EMR portions, the medical professional hovering a cursor over a particular location in the EMR, or the medical professional zooming on the at least a portion of the patient EMR.

5. The method of claim 3, wherein prioritizing the second set of questions comprises prioritizing the second set of questions based on what medications the patient is taking, medication side effects, patient vital signs, or blood test results.

6. The method of claim 1, wherein processing the answers to the second set of questions comprises modifying a form of the answers to be included in a graphical user interface (GUI).

7. The method of claim 1, wherein the GUI presents the answers to the second set of questions in association with the second set of questions.

8. The method of claim 1, wherein the GUI provides links to portions of the patient EMR in association with the answers to the second set of questions.

9. A computer program product comprising a computer readable storage medium having a computer readable program stored therein, wherein the computer readable program, when executed on at least one processor of a data processing system, causes the data processing system to implement a question prediction and answering engine for predicting questions a medical professional is attempting to answer, wherein the computer readable program causes the data processing system to:
  train, by a personalized interaction learning engine, a machine learning model, comprising:
    monitoring interaction of a user with an electronic medical record (EMR) to identify one or more natural language questions entered by the user into an input device and submitted to a cognitive question answering system;
    identifying a first set of questions within a predetermined set of questions that match the one or more natural language questions entered by the user;
    correlating the one or more natural language questions entered by the user to the first set of questions; and
    training the machine learning model based on the correlation between the one or more natural language questions entered by the user and the first set of questions;
  monitor, by an interaction monitoring component executing within the question prediction and answering engine, interaction of a medical professional with a patient electronic medical record (EMR) to identify a medical professional interaction pattern;
  apply, by a question selection component executing within the question prediction and answering engine, the machine learning model to the medical professional interaction pattern to select a second set of questions, from the predetermined set of questions, the medical professional is attempting to obtain an answer to from the patient EMR, wherein the machine learning model is configured to receive the medical professional interaction pattern and determine the set of questions that correlate to the medical professional interaction pattern;

submit, by a question submission component executing within the question prediction and answering engine, the second set of questions to the cognitive question answering system;

receive, by an answer processing component executing within the question prediction and answering engine, answers to the second set of questions from the cognitive question answering system based on the patient EMR;

process, by the answer processing component, the answers to the second set of questions to generate a set of answers to the second set of questions from at least a portion of the patient EMR; and output, by the question prediction and answering engine, a report correlating the second set of questions and the set of answers to the medical professional at least by generating a graphical user interface (GUI) to present the answers to the second set of questions to the medical professional as a tailored, cognitive information retrieval, wherein the GUI presents areas needing additional data retrieval based on questions in the second set of questions for which an answer could not be found in the patient EMR.

10. The computer program product of claim 9, wherein the computer readable program further causes the data processing system to:
determine a context of the interaction of the medical professional with the patient EMR; and
prioritize the second set of questions based on the determined context.

11. The computer program product of claim 9, wherein processing the answers to the second set of questions comprises modifying a form of the answers to be included in a graphical user interface (GUI).

12. An apparatus comprising:
a processor; and
a memory coupled to the processor, wherein the memory comprises instructions which, when executed by the processor, cause the processor to implement a question prediction and answering engine for predicting questions a medical professional is attempting to answer, wherein the instructions cause the processor to:
train, by a personalized interaction learning engine, a machine learning model, comprising:
monitoring interaction of a user with an electronic medical record (EMR) to identify one or more natural language questions entered by the user into an input device and submitted to a cognitive question answering system;
identifying a first set of questions within a predetermined set of questions that match the one or more natural language questions entered by the user;
correlating the one or more natural language questions entered by the user to the first set of questions; and
training the machine learning model based on the correlation between the one or more natural language questions entered by the user and the first set of questions;
monitor, by an interaction monitoring component executing within the question prediction and answering engine, interaction of a medical professional with a patient electronic medical record (EMR) to identify a medical professional interaction pattern;
apply, by a question selection component executing within the question prediction and answering engine, the machine learning model to the medical professional interaction pattern to select a second set of questions, from the predetermined set of questions, the medical professional is attempting to obtain an answer to from the patient EMR, wherein the machine learning model is configured to receive the medical professional interaction pattern and determine the set of questions that correlate to the medical professional interaction pattern;
submit, by a question submission component executing within the question prediction and answering engine, the second set of questions to the cognitive question answering system;
receive, by an answer processing component executing within the question prediction and answering engine, answers to the second set of questions from the cognitive question answering system based on the patient EMR;
process, by the answer processing component, the answers to the second set of questions to generate a set of answers to the second set of questions from at least a portion of the patient EMR; and
output, by the question prediction and answering engine, a report correlating the second set of questions and the set of answers to the medical professional at least by generating a graphical user interface (GUI) to present the answers to the second set of questions to the medical professional as a tailored, cognitive information retrieval, wherein the GUI presents areas needing additional data retrieval based on questions in the second set of questions for which an answer could not be found in the patient EMR.

13. The method of claim 1, wherein identifying the first set of questions comprises:
examining features from the user interaction pattern;
treating the features as if they are evidence passages or portions for candidate answers to a question; and
determining which questions from a predetermined set of questions the evidence passages would answer.

14. The method of claim 1, wherein identifying the first set of questions comprises:
submitting each question from a predetermined set of questions to the cognitive question answering system to determine a set of evidence passages or portions that support an answer to each question; and
determining which sets of evidence passages or portions match the user interaction pattern.

15. The computer program product of claim 9, wherein identifying the first set of questions comprises:
examining features from the user interaction pattern;
treating the features as if they are evidence passages or portions for candidate answers to a question; and
determining which questions from a predetermined set of questions the evidence passages would answer.

16. The computer program product of claim 9, wherein identifying the first set of questions comprises:
submitting each question from a predetermined set of questions to the cognitive question answering system to determine a set of evidence passages or portions that support an answer to each question; and
determining which sets of evidence passages or portions match the user interaction pattern.

17. The apparatus of claim 12, wherein identifying the first set of questions comprises:
examining features from the user interaction pattern;
treating the features as if they are evidence passages or portions for candidate answers to a question; and
determining which questions from a predetermined set of questions the evidence passages would answer.

18. The apparatus of claim 12, wherein identifying the first set of questions comprises:
- submitting each question from a predetermined set of questions to the cognitive question answering system to determine a set of evidence passages or portions that support an answer to each question; and
- determining which sets of evidence passages or portions match the user interaction pattern.

\* \* \* \* \*